United States Patent [19]

Manska

[11] Patent Number: 5,113,571
[45] Date of Patent: May 19, 1992

[54] METHOD OF MANUFACTURING A CONNECTOR FOR MEDICAL DEVICES

[76] Inventor: Wayne E. Manska, 1921 Kellogg Dr., Anaheim, Calif. 92807

[21] Appl. No.: 471,549

[22] Filed: Jan. 29, 1990

[51] Int. Cl.⁵ ............................................. B23P 11/02
[52] U.S. Cl. ...................................... 29/453; 285/332
[58] Field of Search ............... 285/315, 319, 322, 332, 285/354, 386; 29/890.14, 890.141, 453; 604/283, 256, 905

[56] References Cited

U.S. PATENT DOCUMENTS

| | | | |
|---|---|---|---|
| 3,514,131 | 5/1970 | McKinney | 285/332 |
| 3,876,234 | 4/1975 | Harms | 285/332 X |
| 4,076,285 | 2/1978 | Martinez | 285/332 |
| 4,448,470 | 5/1984 | Peterson | 285/319 X |
| 4,452,473 | 6/1984 | Ruschke | 285/386 X |
| 4,639,019 | 1/1987 | Mittleman | 285/332 |
| 4,676,530 | 6/1987 | Nordgren et al. | 285/332 X |
| 4,801,158 | 1/1989 | Gomi | 285/354 X |

OTHER PUBLICATIONS

Kippmed Brochure, Vented & Non-Vented Male Luer Caps.
Kippmed Brochure, Two Piece Male Luer Lock Assembly.
Kippmed Brochure, Female Luer Lock Adaptor.
Kippmed Brochure, Male Luer Lock Adaptor.
Kippmed Brochure, Male Luer Protective Breather Cap (Push-On).
Two drawings showing a non-rotatable luer nut and housing, along with a physical sample of this nut and housing.

*Primary Examiner*—Timothy V. Eley
*Assistant Examiner*—R. Martin
*Attorney, Agent, or Firm*—Knobbe, Martens, Olson & Bear

[57] ABSTRACT

A connector for medical devices includes a housing having an interlock member and two types of luer nuts. One type of luer nut has an interlock member complementary to the interlock member on the housing to prevent rotation of the luer nut about the housing, while another type of luer nut lacks a complementary interlock member, allowing free rotation of the luer nut relative to the housing.

2 Claims, 2 Drawing Sheets

METHOD OF MANUFACTURING A CONNECTOR FOR MEDICAL DEVICES

The present invention relates generally to connectors for medical devices, such as valves, and particularly to connectors having male luer fittings that utilize luer nuts.

Prior art medical devices which have fluid ports typically require connection to fluid lines or other devices. Such fluid ports are usually equipped with connectors which comprise housings having male or female luer fittings. In the case of male luer fittings, a luer nut is mounted on the port housing. The luer nut includes internal threads which are adapted to mate with corresponding external threads on a female luer fitting. By relatively rotating the luer nut with respect to the female luer fitting, the threads draw the male and female fittings together into a fluid-tight engagement.

In most cases, it is desirable that the luer nut rotate with respect to the fluid port housing. Such rotation may be achieved by snap-fitting the luer nut into a groove formed on the housing, such that the luer nut is rotatably mounted in the groove. In certain applications, however, it is desirable to fixedly mount the luer nut so that it cannot rotate relative to the fluid port housing. Commonly, such fixed mounting is accomplished by integrally molding the luer nut with the fluid port housing.

Because there are applications for both rotatable and non-rotatable luer nuts, each medical device is typically manufactured in a rotatable luer nut version and a non-rotatable luer nut version. Manufacture of two versions is expensive since different molds are required for each version. Further, each version must be carried as a separate item of inventory, thereby increasing inventory carrying costs for the medical device.

Accordingly, there is a need in the art for medical devices, such as valves, which can be molded in a single version that is mechanically adapted to yield a connector with either a rotatable luer nut or a non-rotatable luer nut.

SUMMARY OF THE INVENTION

The present invention comprises a connector for a medical device. The connector comprises a housing having an interlock member and a male luer fitting. A luer nut is mounted on the housing to permit the male luer fitting to be fastened to a female luer fitting. Two distinct types of luer nuts are provided. One type of luer nut has an interlock member which is complementary to the interlock member on the housing such that the interlock members engage to prevent the luer nut from rotating with respect to the housing. Another type of luer nut lacks a complementary interlock member and is thus free to rotate around the housing. By selecting the appropriate type of luer nut, the connector can be mechanically adapted to provide either a rotatable luer nut version or a non-rotatable luer nut version.

DETAILED DESCRIPTION OF THE PREFERRED EMBODIMENTS

Figure 1:
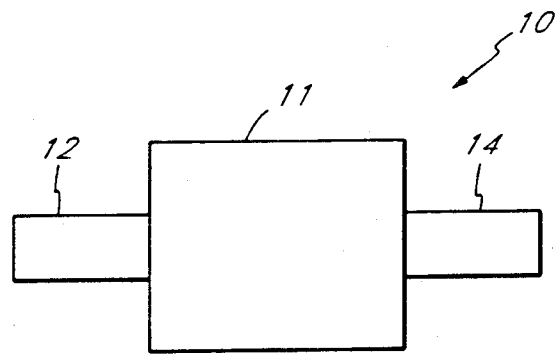
FIG. 1 is a schematic diagram of a medical device having a connector.

As shown schematically in FIG. 1, an exemplary medical device 10 (e.g. a stopcock valve) comprises a main body 11 and two ports 12 and 14 which provide a fluid inlet and fluid outlet for the main body 11. Each port 12, 14 is formed as a connector so that the device 10 can be connected to fluid lines or to other medical devices.

Figure 2:
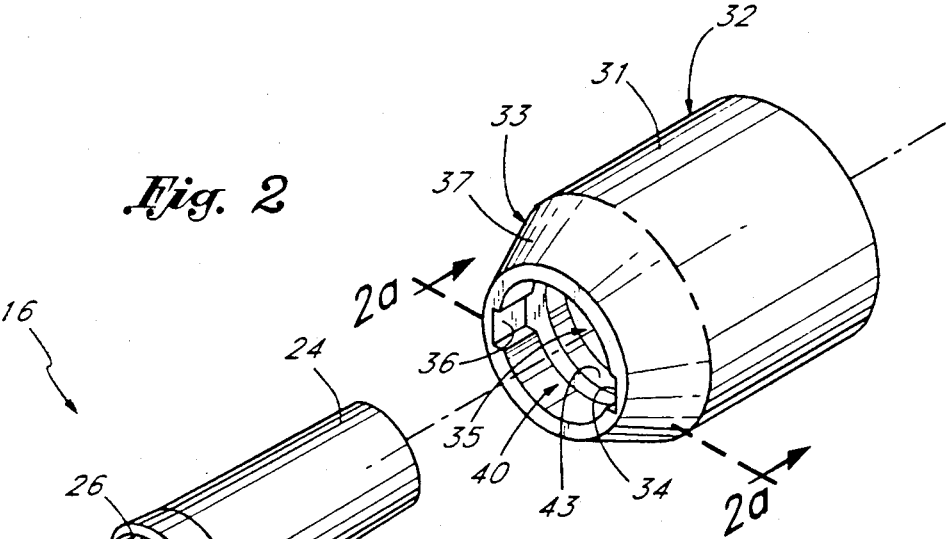
FIG. 2 is an exploded perspective view of a preferred embodiment of the connector of the present invention which utilizes a non-rotatable luer nut.
Figure 3:
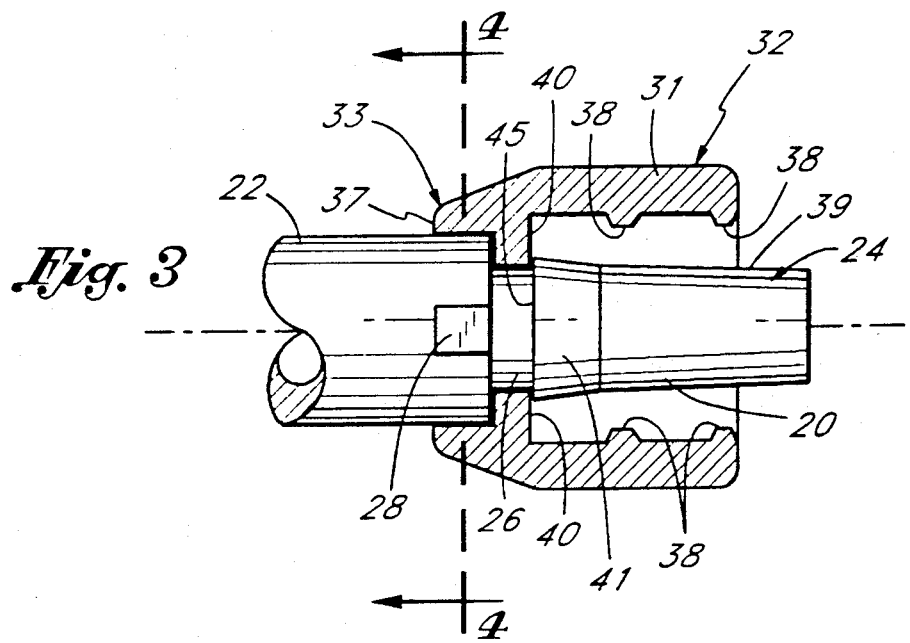
FIG. 3 is an assembled elevation view, in partial cross section, of the connector of FIG. 2 showing the luer nut mounted on the fluid port housing.
Figure 4:
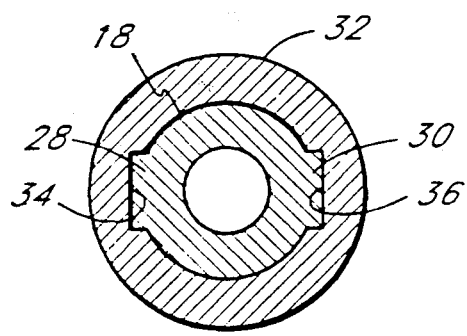
FIG. 4 is a cross sectional view of the connector of FIG. 2 taken along line 4—4 of FIG. 3.

In a preferred embodiment, at least one of the fluid ports 12, 14, comprises a connector 16, as shown in more detail in FIGS. 2, 3, and 4. The connector 16 comprises a fluid port housing 18 having a forward portion 20 and a rearward portion 22, with the forward portion 20 comprising a male luer fitting 24. The housing 18 is integrally molded with the main body 11 to form a single piece device. In addition, the housing 18 is formed as a fluid flow tube having a longitudinal axis 19. A circumferential recess or annular groove 26 is formed on the housing 18 at the juncture between the forward and rearward portions 20, 22, such that the groove 26 is disposed rearward of the male luer fitting 24. The rearward portion 22 of the housing 18 includes an interlock member 27 comprising a surface structure formed by two diametrically spaced tabs 28, 30 which are formed integrally with and protrude from the external surface of the housing 18 as shown in FIG. 2 and FIG. 4. A luer nut 32 having a retaining portion 40 which projects radially inwardly from a body 31 of the nut 32 is mounted on the housing 18, such that the retaining portion 40 is disposed in the annular groove 26. The luer nut 32 has a complementary interlock member 33 comprising a surface structure formed by two slots 34 and 36 in the interior of a rearward protrusion 37 of the luer nut 32. The protrusion 37 is disposed rearwardly of the retaining portion 40 of the nut 32. The two slots 34 and 36 are dimensioned to mate with the tabs 28, 30 on the connector housing 18, so that when the luer nut 32 is mounted on the housing 18, the tabs 28, 30 on the housing 18 engage the slots 34 and 36 in the luer nut 32 and prevent rotation of the luer nut 32 relative to the housing 18. Thus, the tabs 28, 30 provide a lug and the slots 34, 36 provide a mating socket which co-act to fasten the nut 32 to the housing 18 to prevent rotation therebetween.

Figure 2A:
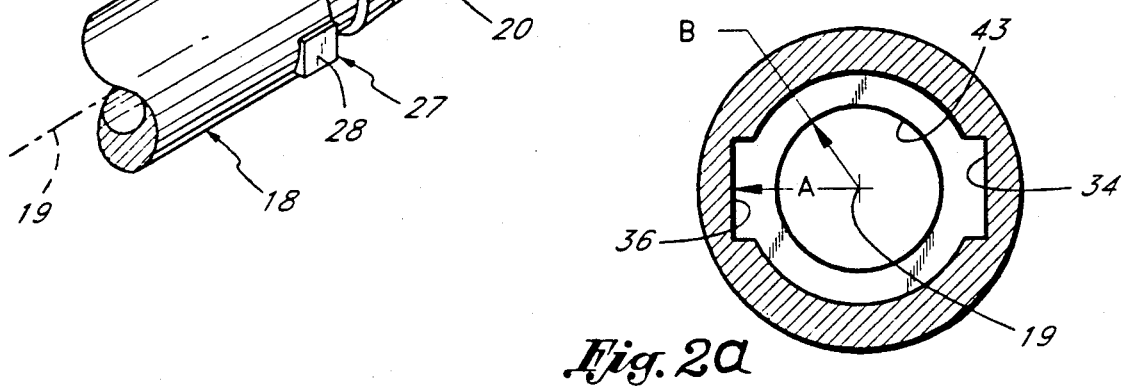
FIG. 2a is a cross-sectional view taken along the lines 2a—2a of FIG. 2.

The male luer fitting 24 comprises a sealing taper portion 39 at its distal end and a lead-in taper portion 41 between the sealing taper portion 39 and the annular groove 26. The sealing taper portion 39 is configured to mate with a complementary sealing taper portion on a female luer fitting (not shown). Referring to FIG. 3, the luer nut 32 includes internal threads 38 which are adapted to mate with external threads on the female luer fitting to permit the sealing taper portions of the male and female luer fittings to be drawn against each other to provide a fluid-tight engagement. The luer nut 32 is mounted on the connector housing 18 by inserting the sealing taper portion 39 through a central opening 35 formed by an interior surface 43 of the retaining portion 40 of the luer nut 32, and sliding the nut 32 over the distal end of the male luer fitting 24 towards the annular groove 26 such that the retaining portion 40 is captured in the groove 26. The interior surface 43 of the central opening 35 is disposed radially outward from the longitudual axis 19. The rearward portion 22 of the housing 18 is substantially larger than the central opening 35 in the luer nut 32 so that the central opening 35 cannot slide over the interlock member 27. The surface structure formed by the slots 34, 36 of the luer nut 32 is disposed radially outward from the longitudinal axis 19 by a distance A which is greater than a distance B from the axis 19 to the interior surface 43 of the central opening 35, as shown in FIG. 2a. The central opening 35 formed by the annular retaining portion 40 on the luer nut 32 is slightly smaller than the lead-in taper portion 41 of the fitting 24 so that the retaining portion 40 snaps over a rearward edge 45 of the lead-in taper portion 41 and into the groove 26. The luer nut 32 and fitting 24 are formed of a plastic material which is sufficiently elastically deformable to permit this snap fit. When mounted on the connector housing 18, the annular groove 26 formed in the housing 18 engages the retaining portion 40 of the luer nut 32, thus axially securing the luer nut 32 on the housing 18.

Figure 5:
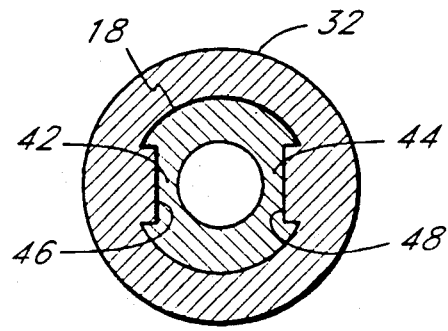
FIGS. 5 and 6 are cross sectional views corresponding to that of FIG. 4 showing alternative embodiments of the present invention.
Figure 6:
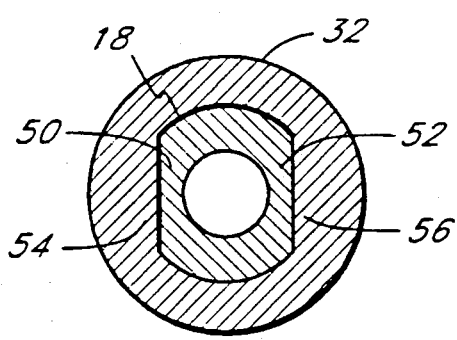

Alternate embodiments of the interlock members 27, 33, are shown in cross section in FIG. 5 and FIG. 6. The interlock member shown in FIG. 5 comprises two diametrically spaced slots 42 and 44 while the complementary interlock member of the luer nut 32 comprises two diametrically spaced tabs 46 and 48 which are dimensioned to mate with the slots 42 and 44 in the housing 18, so as to preclude rotation of the luer nut 32 relative to the housing 18. The interlock member of FIG. 6 comprises two opposing exterior flats 50 and 52 on the housing 18. The complementary interlock member of the luer nut 32 comprises two opposing interior flats 54 and 56 which align with the exterior flats 50 and 52 of the housing 18 to prevent rotation of the luer nut 32 relative to the connector housing 18.

Figure 7:
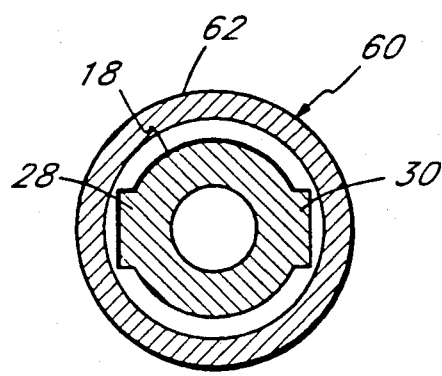
FIG. 7 is a cross sectional view corresponding to that of FIG. 4, showing a preferred embodiment of the present invention which utilizes a rotatable luer nut.

The connector 16 can be mechanically adapted to provide a rotatable luer nut version as shown in FIG. 7. In the embodiment of FIG. 7, the interlock member for the housing 18 is identical to that shown in FIG. 4, comprising two diametrically spaced tabs 28 and 30 which protrude from the external surface of the connector housing 18. A luer nut 60 has a rearward protrusion 62 with an inner diameter which is larger than the maximum diametric distance between the tabs 28 and 30 such that the luer nut 60 is rotatable with respect to the housing 18. Alternatively, the luer nut 60 may be formed without the rearward protrusion 62 and also remain free to rotate about the housing 18.

Although in the preferred embodiments, the interlock member on the housing 18 comprises a lug and the interlock member on the luer nut 32 comprises a socket, those skilled in the art will appreciate that this particular arrangement can be modified so that the interlock member on the housing 18 comprises a socket and the interlock member on the luer nut 32 comprises a lug. It also should be understood that numerous other modifications and embodiments can be devised by those skilled in the art that will fall within the scope of this invention.

What is claimed is:

1. A method of manufacturing a connector for a medical device, comprising:
   (a) providing a first housing having an interlock member and a male luer fitting;
   (b) providing first and second types of luer nuts, said first type of luer nut having an interlock member which is complementary to that of said interlock member on said first housing for engaging with said interlock member on said housing to prevent said first type of luer nut from rotating relative to said first housing, said second type of luer nut lacking a complementary interlock member so as to allow relative rotation between said second type of luer nut and the housing;
   (c) mounting a luer nut of said first type on the first housing such that said interlock member on the first type of luer nut engages the interlock member on the first housing to prevent relative rotation therebetween;
   (d) providing a second housing having an interlock member and a male luer fitting identical to that of said first housing; and
   (e) mounting a luer nut of the second type on the second housing without engaging the interlock member on the second housing, such that said second type of luer nut is rotatable with respect to said housing.

2. The method of claim 1, wherein said mounting step (c) comprises capturing a retaining portion of said first type of luer nut in a circumferential recess disposed between said male luer fitting and said interlock member on said first housing.

* * * * *